United States Patent
Preston et al.

(10) Patent No.: US 11,768,186 B2
(45) Date of Patent: Sep. 26, 2023

(54) HYDROGEN CONCENTRATION SENSOR

(71) Applicant: DOOSAN FUEL CELL AMERICA, INC., South Windsor, CT (US)

(72) Inventors: Joshua Preston, South Windsor, CT (US); Marc Soldini, Seattle, WA (US)

(73) Assignee: HYAXIOM, INC., East Hartford, CT (US)

( * ) Notice: Subject to any disclaimer, the term of this patent is extended or adjusted under 35 U.S.C. 154(b) by 287 days.

(21) Appl. No.: 17/114,746

(22) Filed: Dec. 8, 2020

(65) Prior Publication Data

US 2022/0178893 A1    Jun. 9, 2022

(51) Int. Cl.
*G01N 33/00*     (2006.01)
*H01M 8/0444*    (2016.01)
*H01M 8/04089*   (2016.01)
H01M 8/04746    (2016.01)

(52) U.S. Cl.
CPC ........ *G01N 33/005* (2013.01); *H01M 8/0444* (2013.01); *H01M 8/04089* (2013.01); H01M 8/04753 (2013.01)

(58) Field of Classification Search
USPC ......................................................... 73/23.2
See application file for complete search history.

(56) References Cited

U.S. PATENT DOCUMENTS

| | | | |
|---|---|---|---|
| 3,747,635 A | 7/1973 | Garamy et al. | |
| 3,771,490 A | 11/1973 | Kinney et al. | |
| 4,025,412 A | 5/1977 | LaConti | |
| 4,051,006 A | 9/1977 | Neti et al. | |
| 4,731,211 A | 3/1988 | Lee | |
| 4,766,044 A | 8/1988 | Sederquist | |
| 4,859,305 A | 8/1989 | Schneider et al. | |
| 4,859,307 A | 8/1989 | Nishizawa et al. | |
| 4,895,775 A | 1/1990 | Kato et al. | |

(Continued)

FOREIGN PATENT DOCUMENTS

| CN | 207558943 U | 6/2018 |
|---|---|---|
| JP | H05275097 A | 10/1993 |

(Continued)

OTHER PUBLICATIONS

Translation of JP-2000131273-A (Year: 2000).*

(Continued)

*Primary Examiner* — Nathaniel T Woodward
(74) *Attorney, Agent, or Firm* — Carlson, Gaskey & Olds, P.C.

(57) ABSTRACT

An illustrative example hydrogen concentration sensor includes a first end plate. A hydrogen evolving electrode assembly that generates hydrogen is situated adjacent the first end plate and at least partially exposed through an opening through the end plate. A separator plate is between the hydrogen evolving electrode assembly and a detection electrode assembly. The separator plate includes a passage to allow a flow of hydrogen generated by the hydrogen evolving electrode assembly to the detection electrode assembly. A second end plate is situated adjacent the detection electrode assembly and includes a second opening where a portion of the detection electrode assembly is exposed to a fluid of interest to provide an indication of a concentration of hydrogen in the fluid of interest.

19 Claims, 6 Drawing Sheets

(56) References Cited

U.S. PATENT DOCUMENTS

| | | |
|---|---|---|
| 5,547,554 A | 8/1996 | Kiesele |
| 5,667,653 A | 9/1997 | Schneider et al. |
| 5,668,302 A * | 9/1997 | Finbow .............. G01N 27/404 |
| | | 73/1.06 |
| 6,168,705 B1 | 1/2001 | Molter et al. |
| 6,280,865 B1 | 8/2001 | Eisman et al. |
| 6,368,735 B1 | 4/2002 | Lomax et al. |
| 6,376,124 B1 | 4/2002 | Dodgson et al. |
| 6,455,181 B1 | 9/2002 | Hallum |
| 6,506,296 B2 | 1/2003 | Babes-Dornea et al. |
| 6,558,519 B1 | 5/2003 | Dodgson et al. |
| 6,638,416 B2 | 10/2003 | Wang et al. |
| 6,645,361 B1 | 11/2003 | Bloemer et al. |
| 6,977,121 B2 | 12/2005 | Balliet et al. |
| 6,984,464 B2 | 1/2006 | Margiott et al. |
| 8,298,712 B2 | 10/2012 | Shirakawa |
| 8,840,775 B2 | 9/2014 | Chen et al. |
| 8,932,772 B2 | 1/2015 | Kumei et al. |
| 9,410,919 B2 | 8/2016 | Spong et al. |
| 10,062,915 B2 | 8/2018 | Paganelli |
| 2001/0051290 A1 | 12/2001 | Kashiwagi |
| 2002/0092780 A1 * | 7/2002 | Nadanami .......... G01N 27/4074 |
| | | 205/782 |
| 2003/0158273 A1 | 8/2003 | Kosako et al. |
| 2004/0028967 A1 * | 2/2004 | Katsuki ............ H01M 8/04089 |
| | | 429/432 |
| 2004/0182705 A1 | 9/2004 | Ishikawa et al. |
| 2004/0261500 A1 | 12/2004 | Ng et al. |
| 2005/0042485 A1 | 2/2005 | Murayama |
| 2005/0153180 A1 | 7/2005 | Hsu |
| 2005/0181262 A1 | 8/2005 | Vanderleeden et al. |
| 2005/0214603 A1 | 9/2005 | Barton et al. |
| 2006/0032742 A1 | 2/2006 | Babes-Dornea et al. |
| 2006/0073373 A1 | 4/2006 | Andrin et al. |
| 2008/0145722 A1 | 6/2008 | Coignet et al. |
| 2008/0179199 A1 | 7/2008 | Coignet et al. |
| 2008/0223516 A1 | 9/2008 | Tanuma |
| 2009/0004551 A1 | 1/2009 | Burdzy et al. |
| 2009/0136793 A1 | 5/2009 | Kanno |
| 2009/0166197 A1 | 7/2009 | Grincourt et al. |
| 2010/0028730 A1 | 2/2010 | Ghezel-Ayagh et al. |
| 2011/0151345 A1 | 6/2011 | Lundblad et al. |
| 2014/0251834 A1 | 9/2014 | Chen et al. |
| 2014/0311905 A1 | 10/2014 | Stetter et al. |
| 2017/0025692 A1 | 1/2017 | Zhang et al. |
| 2020/0158683 A1 * | 5/2020 | Preston ................ G01N 27/417 |
| 2020/0350605 A1 * | 11/2020 | Stanescu .......... H01M 8/04776 |

FOREIGN PATENT DOCUMENTS

| | | | |
|---|---|---|---|
| JP | 2000131273 A | * | 5/2000 |
| JP | 2000131273 A | | 5/2000 |
| JP | 2005332610 A | | 12/2005 |
| JP | 2005332610 A2 | | 12/2005 |
| JP | 2009217951 A | | 9/2009 |
| JP | 2014199233 A | | 10/2014 |
| JP | 2015144092 A | | 8/2015 |
| WO | 9409520 | | 4/1994 |
| WO | 2008048270 A1 | | 4/2008 |
| WO | 2011008898 A2 | | 1/2011 |
| WO | 2018209082 A1 | | 11/2018 |
| WO | 2019073850 A1 | | 4/2019 |

OTHER PUBLICATIONS

Cosa+Xentaur, Continuous Hydrogen Analyzer, 2004 COSA Instrument Corporation.

International Search Report and Written Opinion for Application No. PCT/US2020/027136 dated Jul. 28, 2020.

International Search Report and Written Opinion for Application No. PCT/US2019/059768 dated Jan. 21, 2020.

International Search Report and Written Opinion of the International Searching Authority for International application No. PCT/US2021/058217 dated Feb. 8, 2022.

International Search Report and Written Opinion of the International Searching Authority for International application No. PCT/US2021/058186 dated Feb. 8, 2022.

Notice of Preliminary Rejection, Korean Patent Application No. 10-2021-7018973 dated May 31, 2023.

International Preliminary Report on Patentability for International application No. PCT/US2021/058186 dated Jun. 22, 2023.

International Preliminary Report on Patentability for International application No. PCT/US2021/058217 dated Jun. 22, 2023.

* cited by examiner

HYDROGEN CONCENTRATION SENSOR

BACKGROUND

Various devices and processes depend on hydrogen for proper operation. For example, fuel cells typically use hydrogen as a reactant fuel in an electrochemical process to generate electricity. Inadequate hydrogen concentration in the reactant fuel results in unsatisfactory fuel cell performance.

Hydrogen concentration sensors for fuel cells are known. Some such sensors rely on the Nernst Potential across two electrodes induced by a difference in hydrogen concentration at the respective electrodes. One shortcoming of that type of hydrogen sensor is that a reference electrode generates hydrogen as electrical current is applied to the reference electrode. Using the reference electrode to evolve hydrogen in this way tends to introduce potential shifts at the reference electrode, which interferes with accurate hydrogen concentration measurement.

SUMMARY

An illustrative example embodiment of a hydrogen concentration sensor includes a first end plate including a first opening through a portion of the first end plate and a hydrogen evolving electrode assembly situated adjacent the first end plate with at least a portion of the hydrogen evolving electrode assembly exposed through the first opening. The hydrogen evolving electrode assembly is configured to generate hydrogen based on exposure to a fluid at the first opening. At least one separator plate is adjacent the hydrogen evolving electrode assembly on an opposite side of the hydrogen evolving electrode assembly from the first end plate. The separator plate includes a passage configured to allow a flow of hydrogen generated by the hydrogen evolving electrode assembly. A detection electrode assembly is situated adjacent the plate on an opposite side of the separator plate from the hydrogen evolving electrode assembly. At least a portion of the detection electrode assembly is exposed to hydrogen in the passage. A second end plate is adjacent the detection electrode assembly on an opposite side of the detection electrode assembly from the separator plate. The second end plate includes a second opening through a portion of the second end plate. A portion of the detection electrode assembly is exposed to a fluid of interest through the second opening. The detection electrode assembly is configured to provide an indication of a concentration of hydrogen in the fluid of interest.

In an example embodiment having one or more features of the hydrogen concentration sensor of the previous paragraph, the hydrogen evolving electrode assembly comprises first and second electrode layers and a matrix layer between the first and second electrode layers, the detection electrode assembly comprises third and fourth electrode layers and a matrix layer between the third and fourth electrode layers, the first electrode layer is exposed to the first opening, the second electrode layer is at least partially exposed to the passage, the third electrode layer is at least partially exposed to the passage, the fourth electrode layer is exposed to the second opening, and the electrode layers contain a liquid electrolyte.

In an example embodiment having one or more features of the hydrogen concentration sensor of any of the previous paragraphs, the liquid electrolyte comprises phosphoric acid.

In an example embodiment having one or more features of the hydrogen concentration sensor of any of the previous paragraphs includes a heater situated to increase a temperature of at least the liquid electrolyte in the electrode layers.

In an example embodiment having one or more features of the hydrogen concentration sensor of any of the previous paragraphs, the first end plate is electrically conductive; the at least one separator plate is at least partially electrically conductive, the second end plate is electrically conductive; and the hydrogen concentration sensor includes at least one isolating layer between the first end plate and the at least one separator plate, at least one isolating layer between the second end plate and the at least one separator plate, and at least one isolating layer within the at least one separator plate that electrically isolates a first side of the at least one separator plate received against the hydrogen evolving electrode assembly from a second side of the at least one separator plate received against the detection electrode assembly.

In an example embodiment having one or more features of the hydrogen concentration sensor of any of the previous paragraphs, each electrically conductive plate comprises graphite.

In an example embodiment having one or more features of the hydrogen concentration sensor of any of the previous paragraphs, the at least one separator plate comprises two graphite plates, the at least one isolating layer within the at least one separator plate comprises a gasket layer between the two graphite plates, and the gasket includes an opening through the gasket aligned with the passage.

In an example embodiment having one or more features of the hydrogen concentration sensor of any of the previous paragraphs, the isolating layers each comprise a fluoropolymer.

In an example embodiment having one or more features of the hydrogen concentration sensor of any of the previous paragraphs, the at least one isolating layer between the first end plate and the at least one separator plate includes an opening through the at least one isolating layer, the hydrogen evolving electrode assembly is situated within the opening through the at least one isolating layer between the first end plate and the at least one separator plate, the at least one isolating layer between the at least one separator plate and the second end plate includes an opening through the at least one isolating layer, and the detection electrode assembly is situated within the opening through the at least one isolating layer between the at least one separator plate and the second end plate.

In an example embodiment having one or more features of the hydrogen concentration sensor of any of the previous paragraphs, the hydrogen evolving electrode assembly includes two electrode layers and a matrix layer between the two electrode layers, the at least one isolating layer between the first end plate and the at least one separator plate includes three gaskets, one of the two electrode layers is situated in an opening in one of the three gaskets, the other of the two electrode layers is situated in an opening in another one of the three gaskets, and the matrix layer is situated in a middle one of the three gaskets.

In an example embodiment having one or more features of the hydrogen concentration sensor of any of the previous paragraphs, the electrode layers contain a liquid electrolyte, a thickness of the electrode layers has a predetermined relationship to a thickness of the gaskets, and the thickness of the gaskets controls an amount of compression of the electrode layers.

In an example embodiment having one or more features of the hydrogen concentration sensor of any of the previous paragraphs, the at least one separator plate includes a vent situated to allow hydrogen from the passage to exit the hydrogen concentration sensor and the vent is situated to direct hydrogen exiting the vent away from the second opening.

An example embodiment having one or more features of the hydrogen concentration sensor of any of the previous paragraphs includes a housing including a first side received against the first end plate and a second side received against the second end plate, the first side of the housing including a first window aligned with the first opening, the second side of the housing including a second window aligned with the second opening.

In an example embodiment having one or more features of the hydrogen concentration sensor of any of the previous paragraphs, the detection electrode assembly includes two electrode layers and a matrix layer between the two electrode layers and a voltage across the two electrode layers provides the indication of the concentration of hydrogen in the fluid of interest.

An illustrative example embodiment of a method of assembling a hydrogen concentration sensor includes: situating a first end plate adjacent an hydrogen evolving electrode assembly to expose at least a portion of the hydrogen evolving electrode assembly through a first opening through a portion of the first end plate, the hydrogen evolving electrode assembly being configured to generate hydrogen based on exposure to a fluid at the first opening; situating at least one separator plate adjacent the hydrogen evolving electrode assembly on an opposite side of the hydrogen evolving electrode assembly from the first end plate, the at least one separator plate including a passage configured to allow a flow of hydrogen generated by the hydrogen evolving electrode assembly; situating a detection electrode assembly adjacent the at least one separator plate on an opposite side of the at least one separator plate from the hydrogen evolving electrode assembly to position at least a portion of the detection electrode assembly to be exposed to hydrogen in the passage; situating a second end plate adjacent the detection electrode assembly on an opposite side of the detection electrode assembly from the at least one separator plate to position a portion of the detection electrode assembly to be aligned with a second opening through a portion of the second end plate where the portion of the detection electrode assembly can be exposed to a fluid of interest through the second opening, the detection electrode assembly being configured to provide an indication of a concentration of hydrogen in the fluid of interest; and securing the plates and the electrode assemblies in the situated positions.

An example embodiment having one or more features of the method of the previous paragraph includes assembling the hydrogen evolving electrode assembly by situating a first matrix layer between first and second electrode layers, and assembling the detection electrode assembly by situating a second matrix layer between third and fourth electrode layers. The matrix layers and the electrode layers contain a liquid electrolyte.

An example embodiment having one or more features of the method of any of the previous paragraphs includes situating the hydrogen evolving electrode assembly within an opening of at least one gasket that provides a seal around an edge of the assembly to contain the liquid electrolyte and situating the detection electrode assembly within an opening of at least one other gasket that provides a seal around an edge of the assembly to contain the liquid electrolyte.

An example embodiment having one or more features of the method of any of the previous paragraphs includes sealing the at least one gasket to the first end plate on one side of the at least one gasket, sealing the at least one gasket to the at least one separator plate on another side of the at least one gasket, sealing the at least one other gasket to the at least one separator plate on one side of the at least one other gasket, and sealing the at least one other gasket to the second end plate on another side of the at least one other gasket.

An example embodiment having one or more features of the method of any of the previous paragraphs includes positioning a heater near the electrode assemblies to increase a temperature of at least the liquid electrolyte in the electrode layers.

In an example embodiment having one or more features of the method of any of the previous paragraphs, the first end plate is electrically conductive, the at least one separator plate is at least partially electrically conductive, and the second end plate is electrically conductive. The method includes situating at least one isolating layer between the first end plate and the at least one separator plate, situating at least one isolating layer between the second end plate and the at least one separator plate, and including at least one isolating layer within the at least one separator plate that electrically isolates a first side of the at least one separator plate received against the hydrogen evolving electrode assembly from a second side of the at least one separator plate received against the detection electrode assembly.

Various features and advantages of at least one disclosed example embodiment will become apparent to those skilled in the art from the following detailed description. The drawings that accompany the detailed description can be briefly described as follows.

DETAILED DESCRIPTION

Hydrogen concentration sensors designed according to an embodiment of this invention are useful for a variety of purposes. Determining hydrogen concentration for a fuel cell power plant is one example implementation that is discussed below. One feature of embodiments of this invention is that a hydrogen evolving electrode assembly that is distinct from a detection electrode assembly evolves hydrogen into a passage within the sensor construction where the detection electrode assembly is exposed to the evolved hydrogen. The detection electrode assembly is also exposed to a fluid of interest and provides an indication of a concentration of hydrogen in that fluid without requiring any current supply to the detection electrode assembly, which results in improved sensor performance compared to other sensors.

Figure 1:
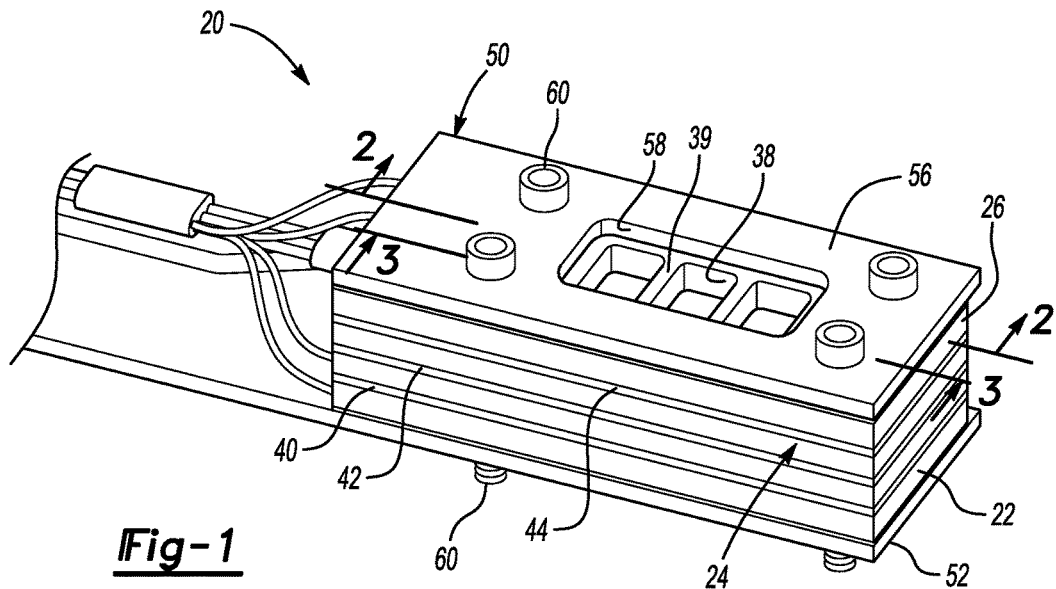
FIG. 1 diagrammatically illustrates an example hydrogen concentration sensor designed according to an embodiment of this invention.
Figure 2:
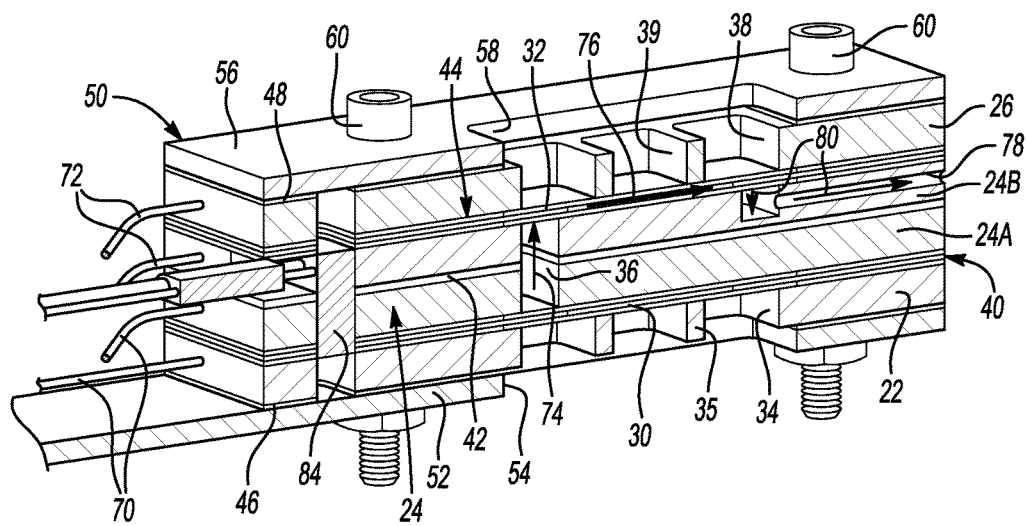
FIG. 2 is a cross-sectional view taken along the lines 2-2 in FIG. 1.
Figure 3:
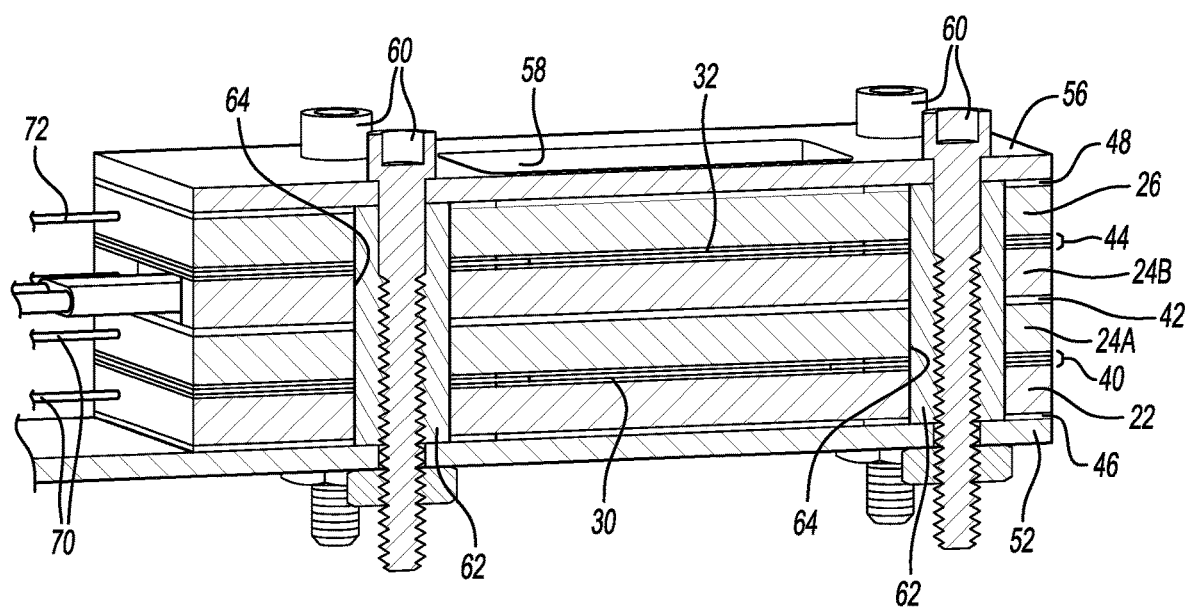
FIG. 3 is a cross-sectional view taken along the lines 3-3 in FIG. 1.

FIGS. 1-3 show an example hydrogen concentration sensor 20. A plurality of components are arranged in a stack including a first end plate 22, at least one multi-layer separator plate 24, and a second end plate 26. A hydrogen evolving electrode assembly 30 is situated between the first end plate 22 and the separator plate 24. A detection electrode assembly 32 is situated between the separator plate 24 and the second end plate 26.

The hydrogen evolving electrode assembly 30 is situated adjacent the first end plate 22 with at least a portion of the hydrogen evolving electrode assembly 30 exposed through a first opening 34 that extends through a portion of the first end plate 22. The hydrogen evolving electrode assembly 30 is configured to generate hydrogen based on exposure to a fluid, such as a gas, at the first opening 34. The hydrogen evolved by the assembly 30 may be pure hydrogen or considered pure for practical purposes even if it is not entirely pure hydrogen.

The first opening 34 includes ribs 35 that provide structural support for the hydrogen evolving electrode assembly 30. The separator plate 24 is on an opposite side of the hydrogen evolving electrode assembly 30 from the first end plate 22. The separator plate 24 includes a passage 36 that allows a flow of evolved hydrogen generated by the hydrogen evolving electrode assembly 30.

The detection electrode assembly 32 is situated adjacent the separator plate 24 on an opposite side of that plate from the hydrogen evolving electrode assembly 30. At least a portion of the detection electrode assembly 32 is exposed to evolved or generated hydrogen in the passage 36. A portion of the detection electrode assembly 32 is exposed to a fluid of interest, such as a gas, through a second opening 38 that extends through the second end plate 26. The second opening 38 includes ribs 29 that provide structural support for the detection electrode assembly 32. The detection electrode assembly 32 provides an indication of a concentration of hydrogen in the fluid of interest present at the opening 38.

The plates 22, 24 and 26 are electrically conductive and, in the illustrated example, comprise graphite. Isolator layers are situated between the plates to electrically isolate them from each other. The isolator layers in the illustrated embodiment also provide a seal at least along a perimeter of the interfaces between the plates. A first isolator layer 40 is situated between the first end plate 22 and the separator plate 24. A second isolator layer 42, which comprises a dielectric material in this embodiment, is situated within the separator plate 24 to electrically isolate opposite sides of the separator plate 24 from each other. In the illustrated example, the multi-layer separator plate 24 includes a first layer or plate 24A and a second layer or plate 24B with the isolator layer 42 between those plates 24A and 24B. One feature of the illustrated example embodiment is that even though the layers 24A and 24B are both at a negative electrical potential, they are kept electrically isolated from each other by the isolator layer 42.

Other embodiments include a different configuration of a separator plate 24 that physically separates the electrode assemblies 30 and 32, provides electrical isolation between the electrode assemblies, and includes electrical isolation between the opposite sides of the separator plate 24.

Another isolation layer 44 is situated between the separator plate 24 and the second end plate 26. The illustrated example embodiment includes isolator layers 46 and 48 between the respective end plates 22 and 26 and a housing 50 that defines an exterior surface of the example sensor 20. The housing 50 includes a first side 52 that is received adjacent the first end plate 22 with the isolating layer 46 between them. The first side 52 includes a first window 54 aligned with the first opening 34, leaving at least a portion of the hydrogen evolving electrode assembly 30 exposed through the window 54 and the opening 34.

A second side 56 of the housing 50 is received adjacent the second end plate 26 with an isolating layer 48 between them. The second side 56 includes a second window 58 aligned with the second opening 38, leaving a portion of the detection electrode assembly 32 exposed through the second window 58 and the second opening 38.

In the illustrated example, each of the isolating layers 40-48 comprises a polymer material that electrically isolates adjacent plates or components from each other. In the illustrated example embodiment, the isolating layers comprise a fluoropolymer. The isolating layers that provide a gas seal are considered a gasket. In some embodiments, the isolating layers that serve as gaskets comprise tetrafluoropolyethylene.

The stack of components and the example housing 50 are secured in a desired alignment by fasteners 60, which in the illustrated example include threaded rods, such as bolts. The fasteners 60 are electrically isolated from the plates 22, 24 and 26 by isolating sleeves 62 that are received in channels 64, which extend through the stack of components as can best be appreciated from FIG. 3. The sleeves 62 comprise a non-conductive material, such as a plastic or polymer.

The sensor 20 includes electrically conductive leads 70 that facilitate applying a voltage to the hydrogen evolving electrode assembly 30. In some example embodiments, the applied voltage is approximately 0.3 volts. The electrical energy carried by the leads 70 is applied to the first end plate 22 and the separator plate 24A. Each of those plates is in electrically conductive contact with the hydrogen evolving electrode assembly 30 and the voltage across the plates 22 and 24A establishes a potential difference across the hydrogen evolving electrode assembly 30.

Additional leads 72 are associated with the detection electrode assembly 32 to allow for measuring a voltage across the detection electrode assembly 32. The measured voltage provides an indication of a concentration of hydrogen in the fluid of interest. The plates 24B and 26 are respectively in electrically conductive contact with the detection electrode assembly 32. The leads 72 are connected with the plates 24B and 26 in this example.

In some embodiments, the device used for measuring the voltage across the detection electrode assembly 32 is a high impedance device to avoid drawing current from the detection electrode assembly 30.

As shown in FIG. 2, hydrogen generated by the hydrogen evolving electrode assembly 30 flows through the passage 36 as represented by the arrow 74. That hydrogen is incident on one side of the detection electrode assembly 32. Because of positive pressure within the passage 36, the hydrogen flows as shown by the arrow 76 along the detection electrode assembly 32 and exits the sensor 20 through a vent 78, which is established in the separator plate 24B in the illustrated example. The arrows 80 represent hydrogen exiting the sensor 20. The vent 78 is situated on a side of the sensor 20 so that hydrogen exiting the vent 78 will not be incident on or near the second window 58 and the second opening 38 to avoid influencing the measured hydrogen concentration in the gas or fluid of interest.

The voltage applied to the hydrogen evolving electrode assembly 32 establishes a pump rate of hydrogen flowing into the passage 36. A sufficiently high flow rate avoids diffusion of gas into the passage 36 from outside of the sensor 20. A sufficient flow rate, which is modulated by the current applied to the electrode assembly 32, establishes positive pressure within the passage 36 and the sensor 20, including along the vent 78

The detection electrode assembly 32 does not have to be provided with any current or reference potential. Instead, the potential developed across the detection electrode assembly 32 results in a voltage that can be measured using the leads 72. The known Nernst Potential phenomenon explains how the potential difference or voltage across the detection electrode assembly 32 corresponds to an indication of a hydrogen concentration in the fluid to which the detection electrode assembly 32 is exposed through the second window 58 in the second opening 38. Given this description and knowledge of the Nernst Potential, those skilled in the art will realize how to obtain a measure of hydrogen concentration based on the voltage of the detection electrode assembly 32.

Figure 4:
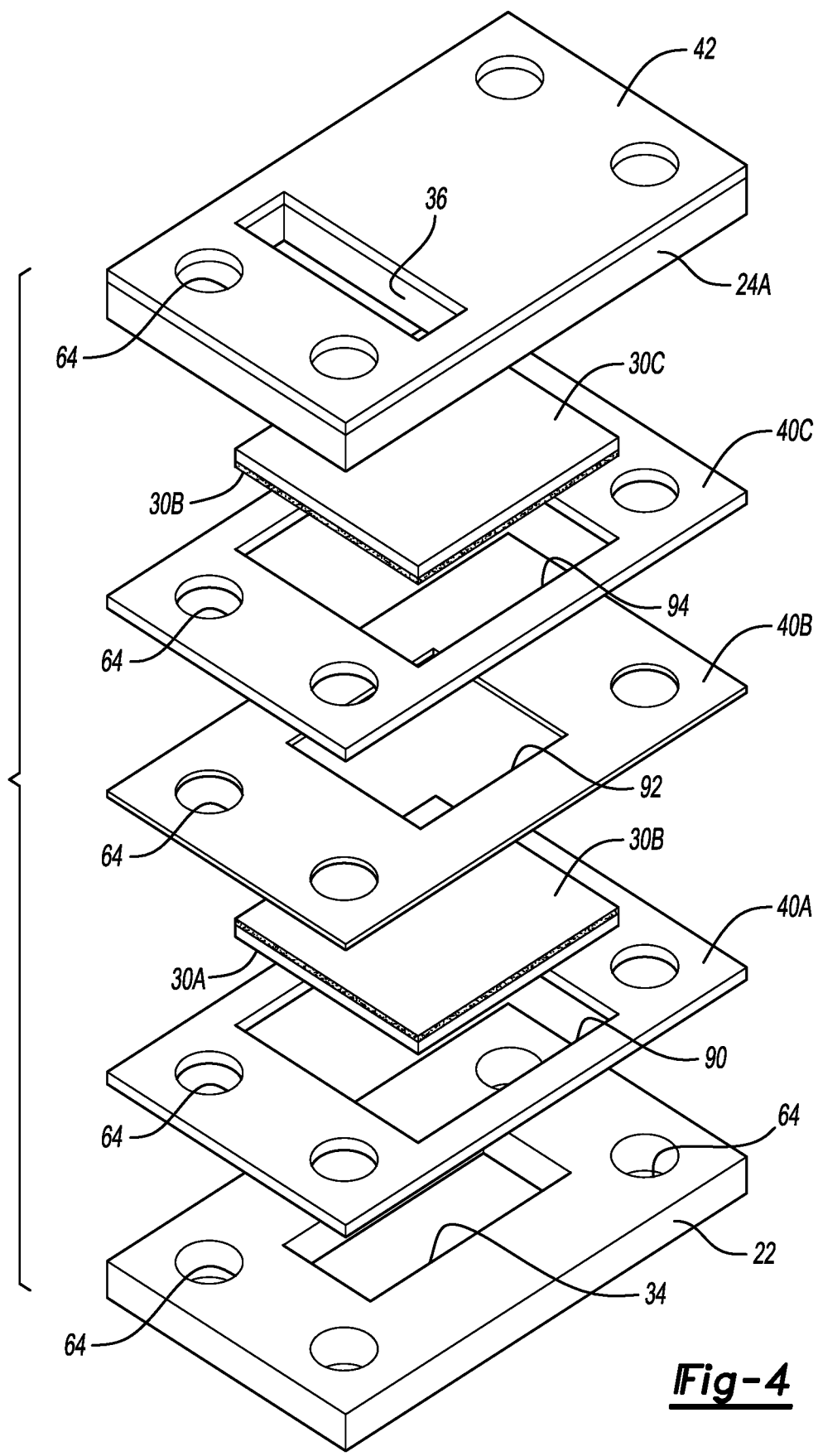
FIG. 4 is an exploded view showing the components of a portion of the embodiment shown in FIG. 1.
Figure 5:
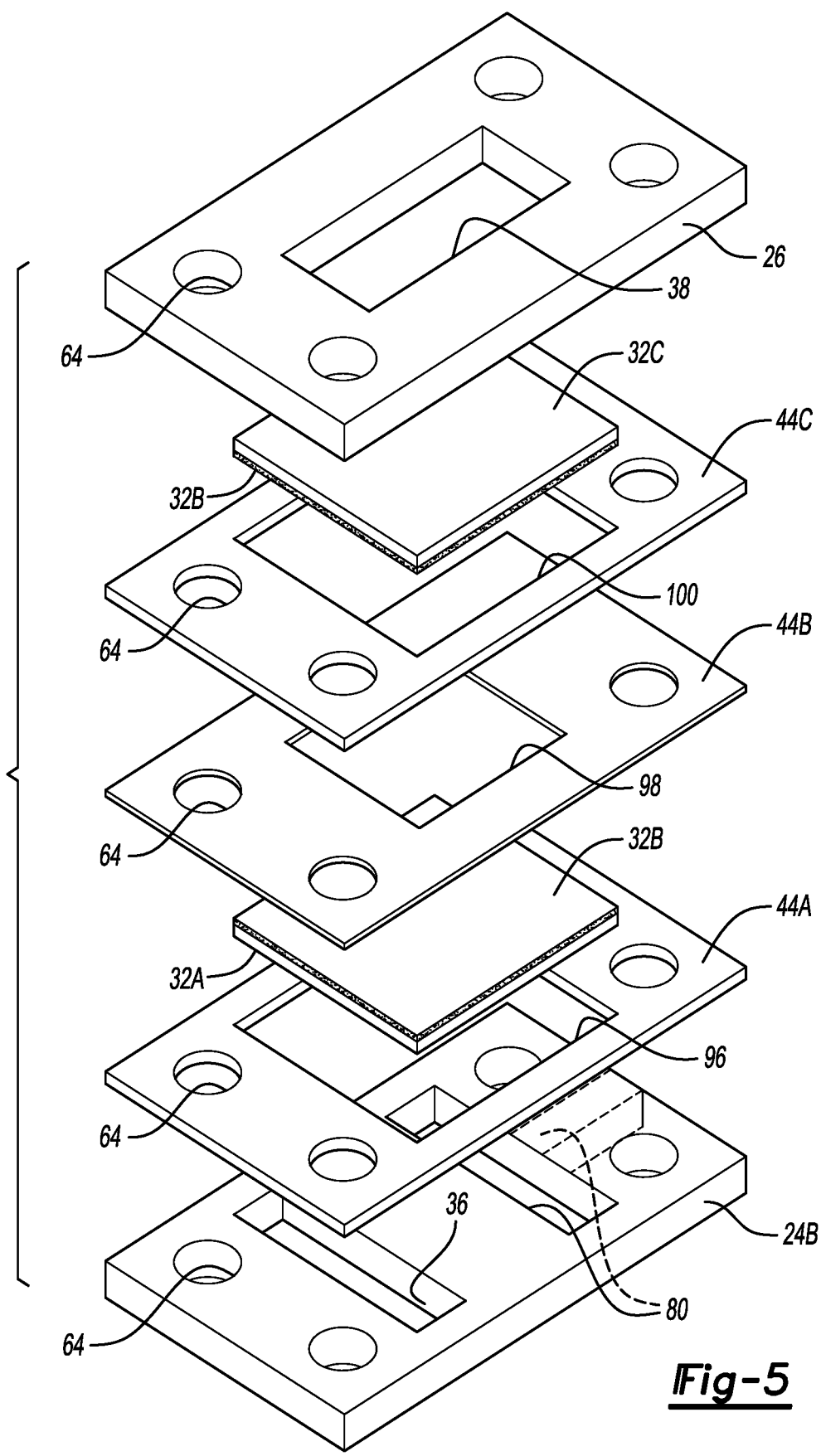
FIG. 5 is an exploded view showing the components of another portion of the embodiment shown in FIG. 1.

FIGS. 4 and 5 are exploded views showing selected features of the components of the example hydrogen sensor 20. The hydrogen evolving electrode assembly 30 in this example includes a first electrode layer 30A and a second electrode layer 30C. In this example, the electrode layers 30A and 30C comprise carbon paper that allows for gas diffusion through each layer. In this embodiment, a matrix layer 30B is established by a relatively thin coating or layer 30B on the sides of the electrode layers 30A and 30C that are received against each other when the sensor 20 is assembled. In the drawing, the coating 30B is applied to the underside of the electrode layer 30C and the upwardly facing side of the electrode layer 30A. Each coating 30B contains a liquid electrolyte, such as phosphoric acid.

In this example, the first electrode layer 30A is a hydrogen oxidizing electrode that is received against and in electrical conductive contact with the first end plate 22. The second electrode layer 30C is a hydrogen evolving electrode that is received against the separator plate 24A and introduces evolved or generated hydrogen into the passage 36.

As can be appreciated from FIG. 4, the isolating layer 40 includes three separate layers or gaskets 40A, 40B and 40C. The first electrode layer 30A is received within a window 90 in the gasket 40A. The gasket 40B includes a window 92 that defines an outer edge and operative area of the matrix layer 30B that is considered active during hydrogen generation. The second electrode layer 30C is received within a window 94 of the gasket 40C.

The thicknesses of the gaskets 40C and 40A control an amount of compression that the electrode layers 30A and 30C experience when the stack of components of the sensor 20 is assembled. Some compression of the electrode layers 30A and 30C is desirable to establish good electrical contact between the electrode layers 30A and 30C, respectively, and the matrix layer 30B. The compression also ensures good electrical contact between the electrode layers 30A, 30C and the plates 22, 24A, respectively. The amount of compression establishes a desired amount of contact while still allowing for gas permeability.

In some embodiments, the gasket 40B does not undergo compression so that the matrix layer 30B within the window 92 is not compressed.

FIG. 5 illustrates some of the components making up the top half (according to the drawings) of the embodiment shown in FIGS. 1-3. In this embodiment, the detection electrode assembly 32 includes a reference electrode layer 32A and a detection electrode layer 32C. A matrix layer 32B is established by coatings on the sides of the electrode layers 32A and 32C that are received against each other. The matrix 32B includes a liquid electrolyte, such as phosphoric acid.

The isolator layer 44 in this example includes three gaskets 44A, 44B and 44C that are received against each other. The electrode layer 32A is received within a window 96 in the gasket 44A. The gasket 44B includes a window 98, which has a smaller area than the window 96. The window 98 establishes an area of the matrix layer 32B while the edges of the gasket 44B seal the edges of the electrode layers 32A and 32C from each other to prevent gas from passing between the electrode layers. The electrode layer 32C is received within a window 100 of the gasket 44C.

The gaskets 44C and 44A have a thickness that controls an amount of compression experienced by the electrode layers 32C and 32A, respectively, once the sensor 20 is assembled. The gasket 44B and the matrix layer 32B received in the window 98 are not compressed in this example.

Each electrode layer 30A, 30C, 32A, 32C in this embodiment comprises a material, such as carbon paper, that has been wetted with a liquid electrolyte, such as phosphoric acid. The matrix layer 30B, 32B of each electrode assembly also contains a liquid electrolyte, such as phosphoric acid.

The housing 50 and the outermost isolating layers 46 and 48, are not shown in FIGS. 4 and 5 even though they are included in the assembled sensor 20.

As seen in FIG. 2, the illustrated example embodiment includes a heater 84 situated to control a temperature of the liquid electrolyte in the electrode assemblies 30 and 32. The heater 84 in this example is situated at least partially within the sensor and accommodated within openings in at least some of the plates 22-26. The heater 84 may heat up the separator plate 24 and the plates 22, 26 to achieve a desired temperature or heating effect on the electrode assemblies 30 and 32 to ensure operation at a desired temperature level.

For example, when the sensor 20 is exposed to a gas stream including acid vapor, it can be useful to keep the sensor 20 at a higher temperature than the temperature of the gas stream. This facilitates maintaining a desired amount of acid in the electrode assemblies 30 and 32. If the sensor 20 were not warmer than the temperature of the gas stream, it may be possible under some conditions for condensation from the gas stream to flood the electrode assemblies 30 and 32 where they are exposed through the openings 34 and 38, for example.

The heater 84 in the illustrated example configuration comprises a material that is not electrically conductive to avoid establishing a short between the different plates or layers of the sensor 20. The heater 84 in some embodiments maintains a sensor temperature above 120° C. This is particularly useful in situations where the sensor is exposed to steam including carbon monoxide, the liquid electrolyte in the hydrogen sensor 20 is phosphoric acid and the sensor 20 is used for determining a concentration of hydrogen in a reformate stream of a hydrogen reformer used to generate fuel for a fuel cell.

Figure 6:
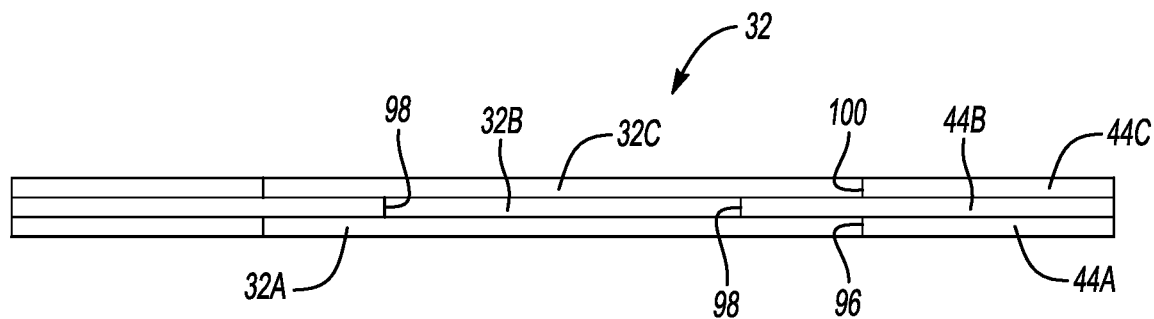
FIG. 6 is a cross-sectional illustration of selected features of an example electrode assembly and associated gaskets.

FIG. 6 shows the arrangement of the detection electrode assembly 32 and the gaskets of the isolating layer 44 in a partial cross-sectional view when the sensor 20 is assembled. The gaskets of the isolating layer 42 and the hydrogen evolving electrode assembly 30 have the same arrangement. The gaskets 44A and 44C include a sealant that establishes a seal around the outside of the detection electrode assembly 32 to prevent unwanted gas migration within the sensor 20. For example, the seal(s) established by the gaskets prevent evolved hydrogen from leaking out of the passage 36 into other portions of the sensor and prevent other gases from reaching the detection electrode layer 32A. In the illustrated example, the gasket 44B does not have sealant.

Figure 7:
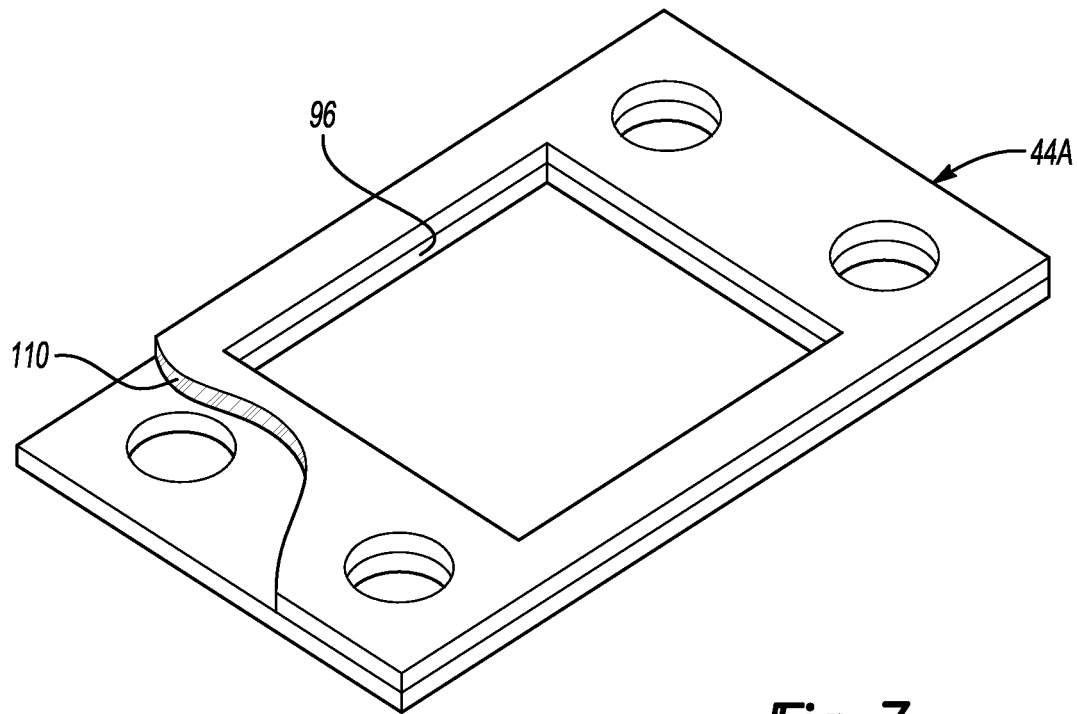
FIG. 7 diagrammatically illustrates an example gasket configuration.

FIG. 7 schematically illustrates a layer of a thermosetting polymer sealant 110 on the exterior of an isolating layer gasket. The gasket 44A is shown in FIG. 7 as an example of the gaskets that include a sealant. A thermosetting polymer sealant adhesively seals the perimeter of the sensor 20 and secures the layers or components of the sensor 20 together. The sealant layer in the illustrated embodiment comprises a fluoropolymer, such as a flouroelastomeric sealant, that is resistant to harsh chemicals, such as phosphoric acid, and is capable of withstanding high temperatures.

Each of the isolating layers 40, 42, 44, 46 and 48 includes an adhesive for sealing at least the perimeter of the interface where each layer is situated in the assembled sensor 20. The fasteners 60 hold all of the components together but the pressure provided by the fasteners 60 is not required to maintain a seal between the components of the sensor 20. The thermosetting polymer seal adhesively seals and secures the layers together including flowing into any defects in a surface of an adjacent layer to achieve a reliable seal. The seals prevent undesired gas penetration into the sensor 20 and undesired gas flow between components in the sensor 20.

According to one example method of making the sensor 20, all of the various layers are situated adjacent each other in the illustrated arrangement and the assembly is heated to at least partially melt the thermosetting polymer sealant, to adhesively seal and secure all of the layers together.

The illustrated example arrangement allows for making a hydrogen concentration sensor in a manner that is economical to produce, provides a reliable sensor configuration, and results in a relatively small sensor size. Example embodiments have dimensions on the order of 50 mm (2 inches) long, 25 mm (1 inch) wide and 25 mm (1 inch) deep.

One feature of the illustrated example is that the reference electrode 32A is distinct from the hydrogen evolving electrode 30C. Using the hydrogen evolving electrode 30C to provide the hydrogen that keeps the reference electrode 32A at a desired reference potential avoids any need to apply current to the reference electrode 32A. This feature eliminates any shifts in the reference potential that would otherwise occur if the reference electrode 32A were used to evolve hydrogen. Having the reference electrode 32A exposed to only hydrogen from the passage 36 also ensures a desired potential resulting from the exposure of the reference electrode 32A to the generated hydrogen.

Figure 8:
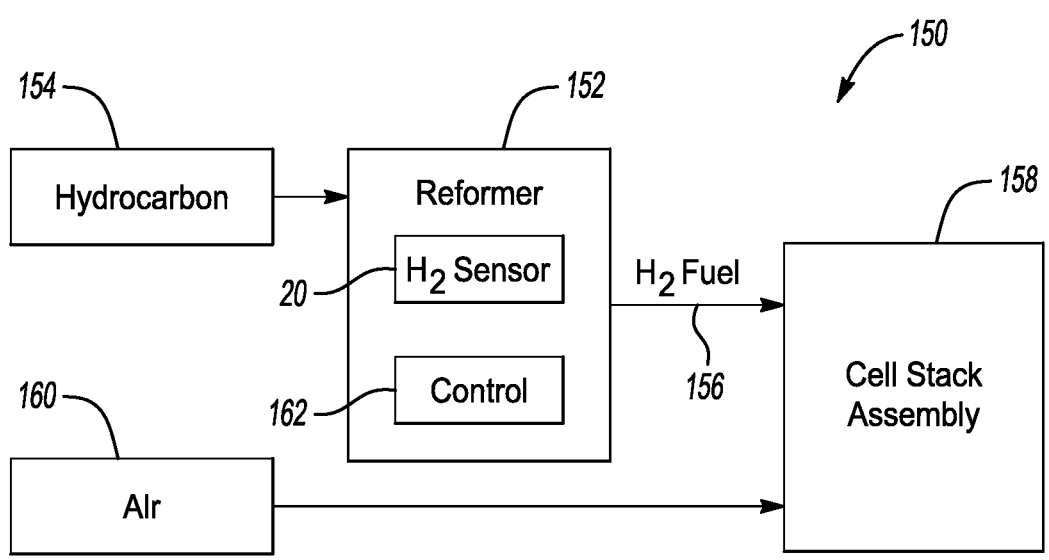
FIG. 8 schematically illustrates selected features of a fuel cell power plant including a hydrogen sensor designed according to an embodiment of this invention.

Hydrogen concentration sensors embodying this invention can be used in a variety of contexts and for various purposes. One example implementation is shown in FIG. 8 in which a sensor 20 is included in a fuel cell power plant 150. A reformer 152 receives a hydrocarbon 154, which may be methane or natural gas for example. The reformer 152 produces a hydrogen fuel at 156 that is supplied to a fuel cell stack assembly 158. The hydrogen fuel is one of the reactants used by the fuel cell stack assembly 158 and oxygen, which may be supplied as air 160, is the other reactant. A hydrogen concentration sensor 20 within the reformer 152 provides information regarding the operation of the reformer 152. A reformer control 162, such as a microprocessor or other computing device, uses the information from the sensor 20 for dynamically adjusting or tuning the operation of the reformer 152. The control 162 does not require any temperature information in this example embodiment, which can provide cost savings compared to systems that require temperature sensors and processing temperature information.

Hydrogen concentration sensors designed according to an embodiment of this invention are more stable and therefore more reliable than previous sensors that utilize a reference electrode that depends on hydrogen to establish the reference potential. Additionally, sensors designed according to an embodiment of this invention can be included in a wider variety of situations where hydrogen level detection is desirable.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

We claim:

1. A hydrogen concentration sensor, comprising:
  a first end plate including a first opening through a portion of the first end plate;
  a hydrogen evolving electrode assembly situated adjacent the first end plate with at least a portion of the hydrogen evolving electrode assembly exposed through the first opening, the hydrogen evolving electrode assembly being configured to generate hydrogen based on exposure to a fluid at the first opening, the hydrogen evolving electrode assembly including first and second electrode layers that each include a coating on one side, the coating comprising a liquid electrolyte;
  at least one separator plate adjacent the hydrogen evolving electrode assembly on an opposite side of the hydrogen evolving electrode assembly from the first end plate, the at least one separator plate including a passage configured to allow a flow of hydrogen generated by the hydrogen evolving electrode assembly;
  a detection electrode assembly situated adjacent the at least one separator plate on an opposite side of the at least one separator plate from the hydrogen evolving electrode assembly, at least a portion of the detection electrode assembly being exposed to hydrogen in the passage, the detection electrode assembly including third and fourth electrode layers that each include a coating on one side, the coating comprising a liquid electrolyte;
  a heater situated to increase a temperature of at least the liquid electrolyte coatings; and
  a second end plate adjacent the detection electrode assembly on an opposite side of the detection electrode assembly from the at least one separator plate, the second end plate including a second opening through a portion of the second end plate, a portion of the detection electrode assembly being exposed to a fluid of interest through the second opening, the detection electrode assembly being configured to provide an indication of a concentration of hydrogen in the fluid of interest.

2. The hydrogen concentration sensor of claim 1, wherein
the coatings on the first and second electrode layers establish a matrix layer between the first and second electrode layers;
the coatings on the third and fourth electrode layers establish a matrix layer between the third and fourth electrode layers;
the first electrode layer is exposed to the first opening;
the second electrode layer is at least partially exposed to the passage;
the third electrode layer is at least partially exposed to the passage.

3. The hydrogen concentration sensor of claim 1, wherein the liquid electrolyte comprises phosphoric acid.

4. The hydrogen concentration sensor of claim 1, wherein
the first end plate is electrically conductive;
the at least one separator plate is at least partially electrically conductive;
the second end plate is electrically conductive; and
the hydrogen concentration sensor includes
at least one isolating layer between the first end plate and the at least one separator plate,
at least one isolating layer between the second end plate and the at least one separator plate, and
at least one isolating layer within the at least one separator plate that electrically isolates a first side of the at least one separator plate received against the hydrogen evolving electrode assembly from a second side of the at least one separator plate received against the detection electrode assembly.

5. The hydrogen concentration sensor of claim 4, wherein each electrically conductive plate comprises graphite.

6. The hydrogen concentration sensor of claim 4, wherein
the at least one separator plate comprises two graphite plates;
the at least one isolating layer within the at least one separator plate comprises a gasket layer between the two graphite plates; and
the gasket includes an opening through the gasket aligned with the passage.

7. The hydrogen concentration sensor of claim 4, wherein the isolating layers each comprise a fluoropolymer.

8. The hydrogen concentration sensor of claim 4, wherein
the at least one isolating layer between the first end plate and the at least one separator plate includes an opening through the at least one isolating layer;
the hydrogen evolving electrode assembly is situated within the opening through the at least one isolating layer between the first end plate and the at least one separator plate;
the at least one isolating layer between the at least one separator plate and the second end plate includes an opening through the at least one isolating layer; and
the detection electrode assembly is situated within the opening through the at least one isolating layer between the at least one separator plate and the second end plate.

9. The hydrogen concentration sensor of claim 8, wherein
the coatings on the first and second electrode layers establish a matrix layer between the first and second electrode layers;
the at least one isolating layer between the first end plate and the at least one separator plate includes three gaskets;
one of the first and second electrode layers is situated at least partially in an opening in one of the three gaskets;
the other of the first and second electrode layers is situated at least partially in an opening in another one of the three gaskets; and
the matrix layer is situated in a middle one of the three gaskets.

10. The hydrogen concentration sensor of claim 9, wherein
a thickness of the electrode layers has a predetermined relationship to a thickness of the gaskets; and
the thickness of the gaskets controls an amount of compression of the electrode layers.

11. The hydrogen concentration sensor of claim 1, wherein
the at least one separator plate includes a vent situated to allow hydrogen from the passage to exit the hydrogen concentration sensor; and
the vent is situated to direct hydrogen exiting the vent away from the second opening.

12. The hydrogen concentration sensor of claim 1, comprising a housing including a first side received against the first end plate and a second side received against the second end plate, the first side of the housing including a first window aligned with the first opening, the second side of the housing including a second window aligned with the second opening.

13. The hydrogen concentration sensor of claim 1, wherein
the coatings on the third and fourth electrode layers establishes a matrix layer between the third and fourth electrode layers; and
a voltage across the third and fourth electrode layers provides the indication of the concentration of hydrogen in the fluid of interest.

14. A method of assembling a hydrogen concentration sensor, the method comprising:
situating a first end plate adjacent an hydrogen evolving electrode assembly to expose at least a portion of the hydrogen evolving electrode assembly through a first opening through a portion of the first end plate, the hydrogen evolving electrode assembly being configured to generate hydrogen based on exposure to a fluid at the first opening, the hydrogen evolving electrode assembly including first and second electrode layers that each include a coating on one side, the coating comprising a liquid electrolyte;
situating at least one separator plate adjacent the hydrogen evolving electrode assembly on an opposite side of the hydrogen evolving electrode assembly from the first end plate, the at least one separator plate including a passage configured to allow a flow of hydrogen generated by the hydrogen evolving electrode assembly;
situating a detection electrode assembly adjacent the at least one separator plate on an opposite side of the at least one separator plate from the hydrogen evolving electrode assembly to position at least a portion of the detection electrode assembly to be exposed to hydrogen in the passage, the detection electrode assembly including third and fourth electrode layers that each include a coating on one side, the coating comprising a liquid electrolyte;
situating a second end plate adjacent the detection electrode assembly on an opposite side of the detection electrode assembly from the at least one separator plate to position a portion of the detection electrode assembly to be aligned with a second opening through a portion of the second end plate where the portion of the detection electrode assembly can be exposed to a fluid of interest through the second opening, the detection electrode assembly being configured to provide an indication of a concentration of hydrogen in the fluid of interest;

positioning a heater near the electrode assemblies to increase a temperature of at least the liquid electrolyte; and securing the plates and the electrode assemblies in the situated positions.

15. The method of claim 14, comprising situating the hydrogen evolving electrode assembly within an opening of at least one gasket that provides a seal around an edge of the assembly to contain the liquid electrolyte; and situating the detection electrode assembly within an opening of at least one other gasket that provides a seal around an edge of the assembly to contain the liquid electrolyte.

16. The method of claim 15, comprising sealing the at least one gasket to the first end plate on one side of the at least one gasket;

sealing the at least one gasket to the at least one separator plate on another side of the at least one gasket;

sealing the at least one other gasket to the at least one separator plate on one side of the at least one other gasket; and sealing the at least one other gasket to the second end plate on another side of the at least one other gasket.

17. The method of claim 14, wherein the first end plate is electrically conductive;

the at least one separator plate is at least partially electrically conductive;

the second end plate is electrically conductive; and the method includes situating at least one isolating layer between the first end plate and the at least one separator plate, situating at least one isolating layer between the second end plate and the at least one separator plate, and including at least one isolating layer within the at least one separator plate that electrically isolates a first side of the at least one separator plate received against the hydrogen evolving electrode assembly from a second side of the at least one separator plate received against the detection electrode assembly.

18. A hydrogen concentration sensor, comprising:

a first end plate including a first opening through a portion of the first end plate;

a hydrogen evolving electrode assembly situated adjacent the first end plate with at least a portion of the hydrogen evolving electrode assembly exposed through the first opening, the hydrogen evolving electrode assembly being configured to generate hydrogen based on exposure to a fluid at the first opening;

at least one separator plate adjacent the hydrogen evolving electrode assembly on an opposite side of the hydrogen evolving electrode assembly from the first end plate, the at least one separator plate including a passage configured to allow a flow of hydrogen generated by the hydrogen evolving electrode assembly;

a detection electrode assembly situated adjacent the at least one separator plate on an opposite side of the at least one separator plate from the hydrogen evolving electrode assembly, at least a portion of the detection electrode assembly being exposed to hydrogen in the passage; and a second end plate adjacent the detection electrode assembly on an opposite side of the detection electrode assembly from the at least one separator plate, the second end plate including a second opening through a portion of the second end plate, a portion of the detection electrode assembly being exposed to a fluid of interest through the second opening, the detection electrode assembly being configured to provide an indication of a concentration of hydrogen in the fluid of interest, wherein:

the hydrogen evolving electrode assembly includes two electrode layers and a matrix layer between the two electrode layers, the at least one isolating layer between the first end plate and the at least one separator plate includes three gaskets, one of the two electrode layers is situated in an opening in one of the three gaskets, the other of the two electrode layers is situated in an opening in another one of the three gasket, and the matrix layer is situated in a middle one of the three gaskets.

19. The hydrogen concentration sensor of claim 18, wherein the electrode layers contain a liquid electrolyte;

a thickness of the electrode layers has a predetermined relationship to a thickness of the gaskets; and the thickness of the gaskets controls an amount of compression of the electrode layers.

* * * * *